(12) United States Patent
Ellinger et al.

(10) Patent No.: US 9,340,487 B2
(45) Date of Patent: May 17, 2016

(54) HALOGENATED DIETHYLTOLUENEDIAMINES

(75) Inventors: Stefan Ellinger, Visp (CH); Gaetano La Delfa, Naters (CH); Constanze Franzke, Ludwigshafen (DE)

(73) Assignee: LONZA LTD., Visp (CH)

( * ) Notice: Subject to any disclaimer, the term of this patent is extended or adjusted under 35 U.S.C. 154(b) by 0 days.

(21) Appl. No.: 13/879,356

(22) PCT Filed: Oct. 11, 2011

(86) PCT No.: PCT/EP2011/005067
§ 371 (c)(1),
(2), (4) Date: Apr. 12, 2013

(87) PCT Pub. No.: WO2012/048845
PCT Pub. Date: Apr. 19, 2012

(65) Prior Publication Data
US 2013/0211142 A1    Aug. 15, 2013

(30) Foreign Application Priority Data
Oct. 14, 2010   (EP) ..................................... 10013629

(51) Int. Cl.
C07C 211/00   (2006.01)
C07C 211/52   (2006.01)
C07C 209/74   (2006.01)
C07C 233/43   (2006.01)

(52) U.S. Cl.
CPC ............. *C07C 211/52* (2013.01); *C07C 209/74* (2013.01); *C07C 233/43* (2013.01)

(58) Field of Classification Search
None
See application file for complete search history.

(56) References Cited

FOREIGN PATENT DOCUMENTS

JP    58-164614 A    9/1983

OTHER PUBLICATIONS

Smith et al. J. Am. Chem. Soc. 1936, 58, 1-10.*
International Search Report of PCT/EP2011/005067 Mailed December 12, 2011.

* cited by examiner

*Primary Examiner* — Clinton Brooks
(74) *Attorney, Agent, or Firm* — MMWV IP, LLC

(57) ABSTRACT

Disclosed are halogenated diethyltoluenediamines of formula

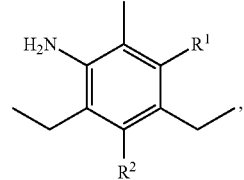

(I)

wherein either $R^1$ is an amino group and $R^2$ is chlorine or bromine, or $R^2$ is an amino group and $R^1$ is chlorine or bromine, and isomeric mixtures thereof. The halogenated diethyltoluenediamines of formula I are useful as chain extenders for polyurethanes and hardeners for epoxy resins having a relatively long gel time.

21 Claims, No Drawings

HALOGENATED DIETHYLTOLUENEDIAMINES

CROSS REFERENCE TO RELATED APPLICATIONS

This application is a §371 National Stage Application of PCT/EP2011/005067, filed Oct. 11, 2011, which claims priority to European Application No. 10013629.0, filed Oct. 14, 2010.

FIELD OF THE INVENTION

The present invention relates to novel chlorinated and brominated diethyltoluenediamines which are suitable as chain extenders or curing agents for polyurethanes and as hardeners for epoxy resins. It further relates to the use of these novel compounds as chain extenders and curing agents for polyurethanes and hardeners for epoxy resins and to processes for the preparation of said halogenated diethyltoluenediamines and novel intermediates in said processes.

BACKGROUND OF THE INVENTION

The use of chain extenders and curing agents for the preparation of polyurethanes and of hardeners for epoxy resins is well known in the art. Polyurethanes, for example, may be obtained by reacting compounds having H-reactive groups such as polyether polyols or polyester polyols with a diisocyanate to form a prepolymer which, in a second step, is then reacted with a curing agent to form the polyurethane. Epoxy resins, on the other hand, may be obtained by reacting epichlorohydrin with an alcohol or phenol to obtain a glycidyl derivative which then is reacted with a hardener to obtain the cured epoxy resin.

The structure of the curing agents and the reactivity of their functional groups are often used to modify the properties of the final product or to control the reaction rate of the polymer formation and the processability of the polymer.

Commonly used chain extenders and curing agents for the preparation of polyurethanes (PU) and epoxy resins are aromatic diamines such as alkyl-substituted and/or chlorinated phenylenediamines or 4,4'-methylene-bisanilines. In the preparation of polyurethanes, the amino groups of these diamines will react with isocyanato groups to give urea moieties. The effect of such compounds on the properties of the polymer system substantially depends on the nature and positions of the alkyl substituents and/or the number and/or positions of the chlorine atoms on the aromatic rings. Sterically hindered diamines such as 4,4'-methylenebis-(3-chloro-2,6-diethylaniline) (M-CDEA) and 4,4'-methylenebis-(2,6-diethylaniline) (M-DEA) are often used as a curing agent. These compounds, however, do not allow easy processing, as their melting point is relatively high. Other well known compounds, such as 4,4'-methylene-bis-(2-chloroaniline) (MOCA) or 3,5-bis(methylthio)toluenediamines (E-300) are toxic and/or malodorous.

It has been an object of the present invention to provide novel aromatic diamines having low toxicity and no offensive odor, combined with moderate reactivity resulting in a convenient gel time (or pot life) when mixed with the urethane prepolymers or epoxy resins. The diamines should also be liquid or semi-liquid at room temperature, or at least easily soluble in the (uncured) epoxy resins, isocyanates and diols used as starting materials in the production of cured epoxy resins and polyurethanes.

SUMMARY OF THE INVENTION

It has been found that halogenated diethyltoluenediamines of formula

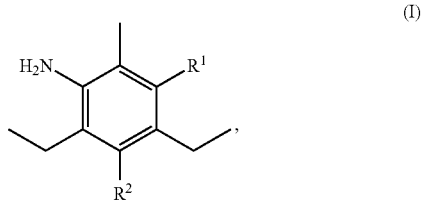

(I)

wherein either $R^1$ is an amino group and $R^2$ is chlorine or bromine, or $R^2$ is an amino group and $R^1$ is chlorine or bromine, and isomeric mixtures thereof are liquid or semi-liquid at room temperature and easily miscible with, or soluble in, the starting materials and prepolymers typically used in the production of polyurethanes and epoxy resins. They further exhibit convenient gel times and are non-malodorous and less toxic than e.g. MOCA. They can be easily synthesized in good yields from commercially available diethyltoluenediamines, either by direct chlorination in sulfuric acid or by bromination of the corresponding diacetyl derivatives, followed by hydrolytic cleavage of the acetyl groups. The brominated diacetyl compounds are novel and also an object of the invention.

DETAILED DESCRIPTION OF THE INVENTION

The invention provides halogenated diethyltoluenediamines of formula

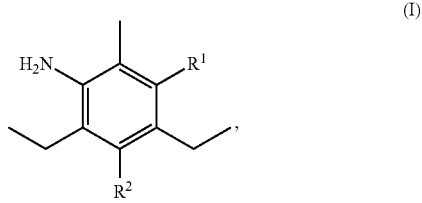

(I)

wherein either $R^1$ is an amino group and $R^2$ is chlorine or bromine or $R^2$ is an amino group and $R^1$ is chlorine or bromine, as well as isomeric mixtures thereof. Isomeric mixtures are preferably those which are obtainable from the commercially available diethyltoluenediamine mixtures, which consist of e.g. about 80% 3,5-diethyltoluene-2,4-diamine and about 20% 3,5-diethyltoluene-2,6-diamine.

According to one preferred embodiment, the halogenated diethyltoluenediamines of formula I are chlorinated, which means that either $R^1$ is an amino group and $R^2$ is chlorine or $R^2$ is an amino group and $R^1$ is chlorine.

According to another preferred embodiment, the halogenated diethyltoluenediamines of formula I are brominated, which means that either $R^1$ is an amino group and $R^2$ is bromine or $R^2$ is an amino group and $R^1$ is bromine, or an isomeric mixture thereof.

Another object of the invention is the use of the halogenated diethyltoluenediamines as chain extenders or curing agents in the production of polyurethanes. Said use is equivalent with a process for the production of a polyurethane by reacting at least one di- or polyfunctional isocyanate with at least one diol or polyol in the presence of, or followed by addition of, at least one of the halogenated diethyltoluenediamines according to the invention.

Still another object of the invention is the use of the halogenated diethyltoluenediamines according to the invention as hardeners (curing agents) for epoxy resins. Said use is equivalent with a process for the production of a cured epoxy resin by reacting at least one di- or polyfunctional epoxide with at least one of the halogenated diethyltoluenediamines according to the invention.

For both applications the pure isomers or isomeric mixtures of the halogenated diethyltoluenediamines of the invention may be used alone or in combination with other amines or mixtures of other amines.

Another object of the invention is a process for the preparation of chlorinated diethyltoluenediamines of formula I, wherein either $R^1$ is an amino group and $R^2$ is chlorine or $R^2$ is an amino group and $R^1$ is chlorine, or isomeric mixtures thereof, comprising the step of reacting a diethyltoluenediamine of formula

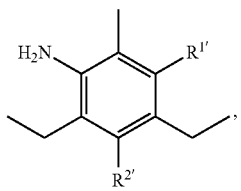

(II)

wherein either $R^{1'}$ is an amino group and $R^{2'}$ is hydrogen, or $R^{2'}$ is an amino group and $R^{1'}$ is hydrogen, or an isomeric mixture thereof, with elemental chlorine in sulfuric acid. The diethyltoluenediamine starting materials of formula II can be used as pure isomers, the preparation of which is disclosed in U.S. Pat. No. 3,275,690, or as an isomeric mixture. Isomeric mixtures are commercially available, for example from Lonza Ltd., Switzerland, under the designation Lonzacure™ DETDA 80 (isomeric mixture of ca. 80% 2,4-di-amino-3,5-diethyltoluene and ca. 20% 2,6-diamino-3,5-diethyltoluene).

The chlorination typically takes place without addition of a catalyst other than sulfuric acid.

In a preferred embodiment of the process for the preparation of chlorinated diethyltoluenediamines of formula I the sulfuric acid is present in an amount of 5 to 50 molar equivalents, based on the amount of diethyltoluenediamine (II).

In another preferred embodiment of the process for the preparation of chlorinated diethyltoluenediamines of formula I the chlorine is added in an amount of 2 to 10 molar equivalents, based on the amount of diethyltoluenediamine (II).

In still another preferred embodiment of the process for the preparation of chlorinated diethyltoluenediamines of formula I the reaction temperature is between 15° C. and 80° C. More preferably, the reaction temperature is between 20° C. and 60° C., for example at about 40° C.

Since the chlorination is carried out with elemental chlorine that is gaseous at the reaction temperature, the reaction is advantageously carried out in a closed vessel, such as an autoclave made of a chlorine-resistant material.

In sulfuric acid the diethyltoluenediamine starting materials of formula II as well as the chlorinated products of formula I are present in protonated form as hydrogensulfates and/or sulfates. During work-up the reaction mixture is neutralized, for example by addition of a strong base such as sodium hydroxide, to obtain the free chlorinated diamines of formula I.

A further object of the invention is a process for the preparation of brominated diethyltoluenediamines of formula I, wherein either $R^1$ is an amino group and $R^2$ is bromine or $R^2$ is an amino group and $R^1$ is bromine, or isomeric mixtures thereof, comprising the steps of
(i) reacting a diethyltoluenediamine of formula

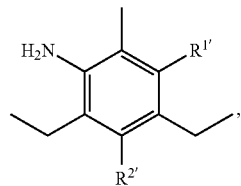

(II)

wherein either $R^{1'}$ is an amino group and $R^{2'}$ is hydrogen, or $R^{2'}$ is an amino group and $R^{1'}$ is hydrogen, or an isomeric mixture thereof, with an acetylating agent to obtain a diacetyl compound of formula

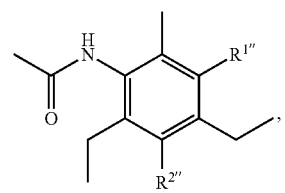

(III)

wherein either $R^{1''}$ is an acetylamino group and $R^{2''}$ is hydrogen or $R^{2''}$ is an acetylamino group and $R^{1''}$ is hydrogen, or an isomeric mixture thereof,
(ii) brominating said diacetyl compound (III) with hydrobromic acid and hydrogen peroxide to obtain a corresponding brominated diacetyl compound of formula

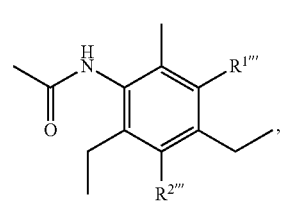

(IV)

wherein either $R^{1'''}$ is an acetylamino group and $R^{2'''}$ is bromine or $R^{2'''}$ is an acetylamino group and $R^{1'''}$ is bromine, or an isomeric mixture thereof, and
(iii) hydrolyzing said brominated diacetyl compound (IV) to obtain the corresponding brominated diethyltoluenediamine (I).

The acetylating agent in step (i) may be any acetylating agent known in the art, for example acetic anhydride or an acetyl halide. In a preferred embodiment of the process for the preparation of brominated diethyltoluenediamines of formula I the acetylating agent in step (i) is acetyl chloride in the presence of triethylamine.

The bromination in step (ii) can take place under relatively mild conditions. In a preferred embodiment of the process for the preparation of brominated diethyltoluenediamines of formula I the bromination step (ii) is conducted at a temperature of −10 to +20° C.

The hydrolysis step (iii) can be conducted under acidic or basic conditions by adding either a strong acid or a strong base. In a preferred embodiment of the process for the preparation of brominated diethyltoluenediamines of formula I the hydrolysis step (iii) is conducted with hydrochloric acid in methanol, thus yielding the corresponding hydrochlorides which are then neutralized by addition of a base to yield the free diamines.

The brominated diacetyl compounds of formula

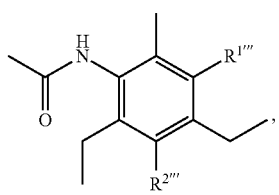

(IV)

wherein either $R^{1'''}$ is an acetylamino group and $R^{2'''}$ is bromine or $R^{2'''}$ is an acetylamino group and $R^{1'''}$ is bromine, or isomeric mixtures thereof, are novel and are likewise an object of the invention.

The following examples, which however are not intended to limit the scope of the invention, will illustrate in more detail selected embodiments and preferred modes of carrying out the invention.

The conversion rates and the product purities were determined by gas chromatography (GC) under the following conditions:

Dimethylpolysiloxane (0.35 μm) column, 30 m×0.32 mm

Temperature program: Starting temperature 130° C., heating rate 1 K/min up to 145° C., then 15 K/min up to 190° C., finally 30 K/min up to 250° C.

Sample preparation: Samples of 0.2 g were dissolved in 1 mL of toluene.

Example 1

6-Chloro-3,5-diethyltoluene-2,4-diamine and 4-chloro-3,5-diethyltoluene-2,6-diamine Lonzacure™ DETDA 80 (isomeric mixture of 80% 3,5-diethyltoluene-2,4-diamine and 20% 3,5-diethyltoluene-2,6-diamine) (3.4 g, 18.6 mmol) and 96 wt % sulfuric acid (28.5 g, 279 mmol) were introduced in an autoclave made of Hastelloy® HC22. The autoclave was heated to 40° C. and flushed with nitrogen. After having released the nitrogen, chlorine gas (5.3 g, 74.4 mmol) was introduced to the mixture. The reaction was stirred at 40° C. for 18 h (reaction time) and then poured onto ice (50 g). The suspension was neutralized with 10% aqueous sodium hydroxide solution (230 g) and after phase separation the aqueous phase was extracted with dichloromethane (50 mL). The combined organic phases were dried over magnesium sulfate and the solvent was evaporated under reduced pressure to give 4.5 g of the isomeric mixture I ($R^1$=Cl, $R^2$=NH$_2$, and $R^1$=NH$_2$, $R^2$=Cl). By GC analysis 96 area % was measured for the isomeric mixture consisting of 6-chloro-3,5-diethyltoluene-2,4-diamine and 4-chloro-3,5-diethyltoluene-2,6-diamine in a 4:1 ratio.

Yield: 3.7 g (93%)

GC retention time data:
$t_R$=12.0 min (3,5-diethyltoluene-2,4-diamine), 13.3 min (3,5-diethyltoluene-2,6-diamine), 18.3 min (6-chloro-3,5-diethyltoluene-2,4-diamine), 18.4 min (4-chloro-3,5-diethyltoluene-2,6-diamine).

Example 2

6-Chloro-3,5-diethyltoluene-2,4-diamine

Example 1 was repeated using pure 3,5-diethyltoluene-2,4-diamine (prepared according to U.S. Pat. No. 3,275,690) instead of Lonzacure™ DETDA 80.

Yield: 3.5 g (88%) $^1$H NMR (DMSO-d$_6$, 500 MHz, 30° C.): δ 4.48 (br. s, 4H), 2.57 (q, J=7.4 Hz, 2H), 2.42 (q, J=7.4 Hz, 2H), 2.06 (s, 3H), 0.99 (t, J=7.4 Hz, 3H), 0.98 (t, J=7.4 Hz, 3H). $^{13}$C NMR (DMSO-d$_6$, 125 MHz, 30° C.): δ 142.38, 141.63, 131.20, 113.92, 110.46, 107.77, 21.42, 17.96, 14.43, 12.98, 11.90.

Example 3

4-Chloro-3,5-diethyltoluene-2,6-diamine

Example 1 was repeated using pure 3,5-diethyltoluene-2,6-diamine (prepared according to U.S. Pat. No. 3,275,690) instead of Lonzacure™ DETDA 80.

Yield: 3.6 g (90%) $^1$H NMR (DMSO-d$_6$, 500 MHz, 30° C.): δ 4.48 (br. s, 4H), 2.56 (q, J=7.4 Hz, 4H), 1.87 (s, 3H), 0.99 (t, J=7.4 Hz, 6H). $^{13}$C NMR (DMSO-d$_6$, 125 MHz, 30° C.): δ 142.25, 130.80, 113.88, 104.50, 21.33, 12.98, 11.33.

Example 4

N,N'-Diacetyl-3,5-diethyltoluene-2,4-diamine and N,N'-diacetyl-3,5-diethyltoluene-2,6-diamine A 2 L three necked round bottomed flask was charged with Lonzacure™ DETDA 80 (120 g, 0.67 mol), triethylamine (179 g, 1.77 mol) and dichloromethane (550 mL). The mixture was cooled to 0° C. and then acetyl chloride (127 g, 1.62 mol) was added dropwise. The mixture was stirred at room temperature for 3.5 h and then it was filtered off and the solid washed with water (3×100 mL). After drying the solid under vacuum, 107 g (61%) of isomeric mixture III ($R^{1'''}$=acetylamino, $R^{2'''}$=H, and $R^{1'''}$=H, $R^{2'''}$=acetylamino) were obtained.

Example 5

N,N'-Diacetyl-3,5-diethyltoluene-2,6-diamine

Example 4 was repeated using pure 3,5-diethyltoluene-2,6-diamine (prepared according to U.S. Pat. No. 3,275,690) instead of Lonzacure™ DETDA 80.

Yield: 105 g (60%) $^1$H NMR (DMSO-d$_6$, 500 MHz, 30° C.): δ 9.17 (br. s, 2H), 6.92 (s, 1H), 2.46 (q, J=7.4 Hz, 4H), 2.01 (s, 6H), 1.95 (s, 3H), 1.08 (t, J=7.4 Hz, 6H). $^{13}$C NMR (DMSO-d$_6$, 125 MHz, 30° C.): δ 168.21, 139.40, 133.65, 132.73, 125.12, 24.38, 22.40, 14.48, 13.49.

Example 6

N,N'-Diacetyl-3,5-diethyltoluene-2,4-diamine

Example 4 was repeated using pure 3,5-diethyltoluene-2,4-diamine (prepared according to U.S. Pat. No. 3,275,690) instead of Lonzacure™ DETDA 80.

Yield: 111 g (62%) $^1$H NMR (DMSO-$d_6$, 500 MHz, 30° C.): δ 9.17 (br. s, 2H), 6.93 (s, 1H), 2.42 (m, 4H), 2.07 (s, 3H), 2.01 (s, 6H), 1.09 (t, J=7.4 Hz, 3H), 0.93 (t, J=7.4 Hz, 3H). $^{13}$C NMR (DMSO-$d_6$, 125 MHz, 30° C.): δ 168.67, 168.31, 139.93, 139.27, 134.52, 132.96, 132.29, 126.98, 24.18, 22.40, 20.84, 17.91, 14.40, 13.87.

Example 7

N,N'-Diacetyl-6-bromo-3,5-diethyltoluene-2,4-diamine and N,N'-diacetyl-4-bromo-3,5-diethyltoluene-2,6-diamine Aqueous hydrobromic acid (40 wt % HBr, 493 g, 2.44 mol) was added dropwise to a solution of isomeric mixture of III (prepared according to Example 4) (40 g, 0.15 mol) in methanol (650 mL) at 0° C. Aqueous hydrogen peroxide (30 wt % $H_2O_2$, 259 g, 2.29 mol) was then added at 0° C. and the reaction mixture was allowed to warm up to room temperature overnight. The yellow reaction mixture was quenched with saturated aqueous $NaHSO_3$, filtered off and washed with water. The solid was dried under vacuum to give 41 g (79%) of isomeric mixture IV ($R^{1'''}$=acetylamino, $R^{2'''}$=Br, and $R^{1'''}$=Br, $R^{2'''}$=acetylamino).

Example 8

N,N'-Diacetyl-6-bromo-3,5-diethyltoluene-2,4-diamine

Example 7 was repeated using N,N'-diacetyl-3,5-diethyltoluene-2,4-diamine (prepared according to Example 6) instead of isomeric mixture III.

Yield: 46 g (62%) $^1$H NMR (DMSO-$d_6$, 500 MHz, 80° C.): δ 9.17 (br. s, 2H), 2.70 (br. m, 2H), 2.42 (br. m, 2H), 2.22 (s, 3H), 2.03 (s, 6H), 1.07 (t, J=7.5 Hz, 3H), 0.95 (t, J=7.5 Hz, 3H). $^{13}$C NMR (DMSO-$d_6$, 125 MHz, 30° C.): δ 169.03, 140.30, 139.68, 135.37, 134.02, 133.39, 123.88, 26.20, 22.36, 21.18, 19.55, 13.52, 13.02.

Example 9

N,N'-Diacetyl-4-bromo-3,5-diethyltoluene-2,6-diamine

Example 7 was repeated using N,N'-diacetyl-3,5-diethyltoluene-2,6-diamine (prepared according to Example 5) instead of isomeric mixture III.

Yield: 43 g (60%) $^1$H NMR (DMSO-$d_6$, 500 MHz, 80° C.): δ 9.17 (br. s, 2H), 2.70 (br. m, 4H), 2.01 (s, 6H), 1.91 (s, 3H), 1.06 (t, J=7.4 Hz, 3H). $^{13}$C NMR (DMSO-$d_6$, 125 MHz, 30° C.): δ 168.55, 139.98, 134.71, 134.02, 122.72, 26.15, 22.32, 13.65, 13.09.

Example 10

6-Bromo-3,5-diethyltoluene-2,4-diamine and 4-bromo-3,5-diethyltoluene-2,6-diamine The isomeric mixture IV (prepared according to Example 7) (30 g, 0.09 mol), methanol (250 mL) and concentrated hydrochloric acid (360 mL) were charged into a flask and the mixture was heated at reflux for 120 h. After cooling to room temperature, the mixture was concentrated under vacuum. Water was added to dissolve the solid, the pH was adjusted to ~9 with aqueous sodium hydroxide and the product was extracted with dichloromethane. The organic layer was concentrated and the crude product was purified by flash column chromatography to give 15 g (65%) of isomeric mixture of I ($R^1$=$NH_2$, $R^2$=Br, and $R^1$=Br, $R^2$=$NH_2$).

$^1$H NMR (DMSO-$d_6$, 500 MHz, 30° C.): δ 4.39 (br. s, 4H), 2.67-2.62 (m, ~2.4H), 2.44-2.40 (m, ~1.6H), 2.13 (s, ~2.4H), 1.85 (s, ~0.6H), 1.00-0.97 (m, 6H).

Example 11

6-Bromo-3,5-diethyltoluene-2,4-diamine

Example 10 was repeated using N,N'-diacetyl-3,5-diethyltoluene-2,4-diamine (prepared according to EXAMPLE 8) instead of the isomeric mixture of IV.

Yield: 14 g (61%) $^1$H NMR (DMSO-$d_6$, 500 MHz, 30° C.): δ 4.38 (br. s, 4H), 2.65 (q, J=7.4 Hz, 2H), 2.44 (q, J=7.4 Hz, 2H), 2.13 (s, 3H), 0.99 (t, J=7.4 Hz, 3H), 0.98 (t, J=7.4 Hz, 3H). $^{13}$C NMR (DMSO-$d_6$, 125 MHz, 30° C.): δ 142.60, 141.84, 125.38, 115.38, 110.94, 109.42, 24.60, 18.03, 17.92, 12.88, 11.77.

Example 12

4-Bromo-3,5-diethyltoluene-2,6-diamine

Example 10 was repeated using N,N'-diacetyl-3,5-diethyltoluene-2,6-diamine (prepared according to Example 9) instead of the isomeric mixture of IV.

Yield: 12.5 g (54%) $^1$H NMR (DMSO-$d_6$, 500 MHz, 30° C.): δ 4.48 (br. s, 4H), 2.64 (q, J=7.4 Hz, 4H), 1.86 (s, 3H), 0.99 (t, J=7.4 Hz, 6H). $^{13}$C NMR (DMSO-$d_6$, 125 MHz, 30° C.): δ 142.50, 124.82, 115.28, 104.96, 24.50, 12.88, 11.36.

Use of the Halogenated Diethyltoluenediamines as Chain Extenders and Curing Agents for Polyurethanes and as Hardeners for Epoxy Resins:

Abbreviations:
DETDA=3,5-Diethyltoluenediamines (mixture of 80% 2,4- and 20% 2,6-diamine)
DETDA-Cl=Chloro-3,5-diethyltoluenediamines (prepared according to Example 1)
DETDA-Br=Bromo-3,5-diethyltoluenediamines (prepared according to Example 10)
M-DEA=4,4'-Methylenebis(2,6-diethylaniline)
M-CDEA=4,4'-Methylenebis(3-chloro-2,6-diethylaniline)
MOCA=4,4'-Methylenebis(2-chloroaniline)
E-300=3,5-Bis(methylthio)toluenediamines (isomeric mixture of 2,4- and 2,6-diamine)

The new chain extenders and curing agents I for polyurethanes and epoxies show an increase of the gel time as compared to DETDA. As these amines are liquid/semi crystalline at room temperature, they can be processed at much lower temperatures as compared to other aromatic amines (M-DEA, M-CDEA, MOCA).

If I is mixed with the diol Voranol® EP 1900 (polyetherdiol based on polypropylene glycol with an OH number of 26-29 and a $M_w$ of 3800 g/mol from DOW) in the ratio between 25% and 75% and reacted with the isocyanate Suprasec® 2008 (prepolymerized diphenylmethane diisocyanate (MDI) with an isocyanate value of 10.2%, an average functionality of 2.0 and a viscosity of 1800 mPa·s at 25° C., available from Huntsman Polyurethanes), an increase of the gel time is detected compared to DETDA. On the amine market, E-300, MOCA and M-CDEA are the amines with long gel times, therefore these results were compared with those of the halogenated diethyltoluenediamines of the present invention.

Example 13

Polyurethane Gel Time Measurements

The halogenated diethyltoluenediamines according to the invention were used as chain extenders and curing agents in polyurethane formulations. They were dissolved and pre-mixed in Voranol® EP-1900 at a temperature of 20° C. up to 50° C., followed by a quick mixing. The solution was then allowed to cool down to room temperature. Then the isocyanate Suprasec® 2008 was added. The molar ratio of isocyanate groups to the sum of amino and hydroxy groups was 95:100 in all tests. The gel time was measured at 25° C. using a Gelnorm® gel timer (Gel Instrumente AG, Thalwil, Switzerland) according to DIN 16945. For comparison purposes the gel times of similar formulations with the known curing agents DETDA, E-300, M-CDEA and MOCA have also been determined. The results are compiled in Table 1 below. (Tests Nos. C1-C13 are comparative tests.)

The results show a quite substantial increase of the gel time as compared to the non-halogenated DETDA. The range of obtainable gel times is significantly wider than with M-CDEA, which provides the used with more flexibility in processing the polyurethane formulations.

TABLE 1

| Test No. | Amine Type/Amount [g] | Diol [g] | Isocyanate [g] | Amine/Diol Ratio (NH$_2$:OH Molar Equivalents) | Gel Time @ 25° C. [s] |
|---|---|---|---|---|---|
| C1 | DETDA/0.43 | 3.26 | 2.50 | 75/25 | 10 |
| C2 | DETDA/0.19 | 4.35 | 1.67 | 50/50 | * |
| C3 | DETDA/0.08 | 5.45 | 1.39 | 25/75 | * |
| C4 | E-300/0.51 | 3.26 | 2.50 | 75/25 | 780 |
| C5 | E-300/0.23 | 4.35 | 1.67 | 50/50 | 2280 |
| C6 | E-300/0.09 | 5.45 | 1.39 | 25/75 | 10300 |
| C7 | M-CDEA/0.91 | 3.26 | 2.50 | 75/25 | 110 |
| C8 | M-CDEA/0.40 | 4.35 | 1.67 | 50/50 | 250 |
| C9 | M-CDEA/0.15 | 4.91 | 1.25 | 25/75 | 358 |
| C10 | MOCA/0.64 | 3.26 | 2.50 | 75/25 | 1860 |
| C11 | MOCA/0.32 | 4.90 | 1.88 | 50/50 | 27480 |
| C12 | MOCA/0.11 | 4.91 | 1.25 | 25/75 | 108000 |
| 1 | DETDA-Br/0.51 | 2.72 | 2.08 | 75/25 | 70 |
| 2 | DETDA-Br/0.27 | 4.35 | 1.67 | 50/50 | 240 |
| 3 | DETDA-Br/0.10 | 4.91 | 1.25 | 25/75 | 940 |
| 4 | DETDA-Cl/0.43 | 2.72 | 2.08 | 75/25 | 89 |
| 5 | DETDA-Cl/0.23 | 4.35 | 1.67 | 50/50 | 184 |
| 6 | DETDA-Cl/0.09 | 4.91 | 1.25 | 25/75 | 1210 |
| C13 | none | 5.49 | 1.39 | 0/100 | 108000 |

* Too reactive, not possible to determine.

Example 14

Epoxy Resin Gel Time Measurements

The gel time in epoxies was measured as follows:
Bisphenol A diglycidyl ether (produced from bisphenol A and epichlorohydrin, commercially available as Epikote™ 828 EL, Hexion Specialty Chemicals (Columbus Ohio, USA) was mixed at 40° C. with the viscous halogenated diethyltoluenediamine of formula I (DETDA-Br and DETDA-Cl). The amounts of epoxy resin and curing agent were chosen to obtain a molar ratio of epoxy groups to amino groups of 1:1. The mixture was stirred to obtain a homogeneous viscous solution and then cooled to 25° C. The gel times of the viscous preparations were determined using a Gelnorm® gel timer (Gel Instrumente AG, Thalwil, Switzerland) according to DIN 16945 at 130° C., 150° C. and 180° C. For comparison purposes the tests were repeated with E-300, M-CDEA, MOCA and DETDA (Test Nos. C14-C17). The results are compiled in Table 2 below.

TABLE 2

| Test No. | Amine Type/Amount [g] | Epikote™ 828 EL [g] | Gel Time [min] @ 130° C. | Gel Time [min] @ 150° C. | Gel Time [min] @ 180° C. |
|---|---|---|---|---|---|
| 7 | DETDA-Br/6.43 | 18.6 | 179 | 89 | 32 |
| 8 | DETDA-Cl/5.32 | 18.6 | 156 | 78 | 28 |
| C14 | E-300/3.76 | 18.6 | 264 | 116 | 34 |
| C15 | M-CDEA/9.48 | 18.6 | 265 | 128 | 48 |
| C16 | MOCA/6.68 | 18.6 | 129 | 60 | 19 |
| C17 | DETDA/4.46 | 18.6 | 32 | 14 | 5 |

The invention claimed is:

1. A halogenated diethyltoluenediamine of formula

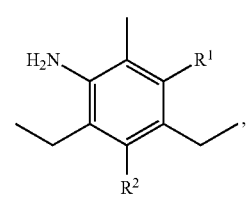

(I)

wherein either R$^1$ is an amino group and R$^2$ is chlorine or bromine or R$^2$ is an amino group and R$^1$ is chlorine or bromine, and/or an isomeric mixture thereof.

2. The halogenated diethyltoluenediamine of claim 1, wherein either R$^1$ is an amino group and R$^2$ is chlorine or R$^2$ is an amino group and R$^1$ is chlorine, and/or an isomeric mixture thereof.

3. The halogenated diethyltoluenediamine of claim 1, wherein either $R^1$ is an amino group and $R^2$ is bromine or $R^2$ is an amino group and $R^1$ is bromine, and/or an isomeric mixture thereof.

4. The halogenated diethyltoluenediamine according to claim 1 adapted for use as a chain extender and/or curing agent in production of polyurethane.

5. The halogenated diethyltoluenediamine according to claim 1 adapted for use as a hardener for an epoxy resin.

6. A process for preparing the halogenated diethyltoluenediamine according to claim 2, comprising reacting a diethyltoluenediamine of formula

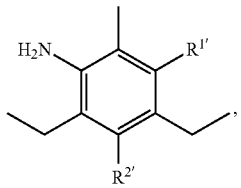

(II)

wherein either $R^{1'}$ is an amino group and $R^{2'}$ is hydrogen, or $R^{2'}$ is an amino group and $R^{1'}$ is hydrogen,
and/or an isomeric mixture thereof,
with chlorine in sulfuric acid.

7. The process of claim 6, wherein the sulfuric acid is present in an amount of 5 to 50 molar equivalents, based on the amount of diethyltoluenediamine (II).

8. The process of claim 6, wherein the chlorine is added in an amount of 2 to 10 molar equivalents, based on the amount of diethyltoluenediamine (II).

9. The process of claim 6, wherein the reacting is conducted at a temperature from 15° C. to 80° C.

10. A process for preparing the halogenated diethyltoluenediamine according to claim 3, comprising
(i) reacting a diethyltoluenediamine of formula

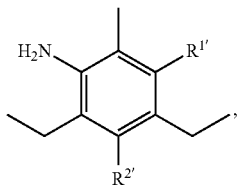

(II)

wherein either $R^{1'}$ is an amino group and $R^{2'}$ is hydrogen, or $R^{2'}$ is an amino group and $R^{1'}$ is hydrogen,
and/or an isomeric mixture thereof,
with an acetylating agent to obtain a diacetyl compound of formula

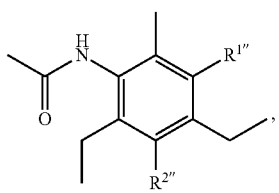

(III)

wherein either $R^{1''}$ is an acetylamino group and $R^{2''}$ is hydrogen or $R^{2''}$ is an acetylamino group and $R^{1''}$ is hydrogen,
and/or an isomeric mixture thereof,
(ii) brominating said diacetyl compound (III) with hydrobromic acid and hydrogen peroxide to obtain a corresponding brominated diacetyl compound of formula

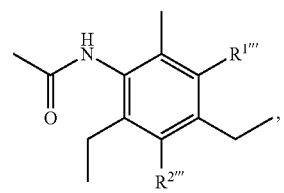

(IV)

wherein either $R^{1'''}$ an acetylamino group and $R^{2'''}$ bromine or $R^{2'''}$ an acetylamino group and $R^{1'''}$ is bromine,
and/or an isomeric mixture thereof, and
(iii) hydrolyzing said brominated diacetyl compound (IV) to obtain said halogenated diethyltoluenediamine (I).

11. The process of claim 10, wherein the acetylating agent in (i) is acetyl chloride in the presence of triethylamine.

12. The process of claim 10, wherein the brominating (ii) is conducted at a temperature of −10 to +20° C.

13. The process of claim 10, wherein the hydrolyzing (iii) is conducted with hydrochloric acid in methanol.

14. A chain extender and/or curing agent for producing polyurethane comprising the halogenated diethyltoluenediamine according to claim 1.

15. A polyurethane produced with a chain extender and/or curing according to claim 14.

16. A hardener for an epoxy resin comprising a halogenated diethyltoluenediamine according to claim 1.

17. An epoxy resin hardened with a hardener according to claim 16.

18. The halogenated diethyltoluenediamine according to claim 1, which is liquid or semi-liquid at room temperature.

19. The halogenated diethyltoluenediamine according to claim 1, which is an isomeric mixture.

20. A brominated diacetyl compound of formula

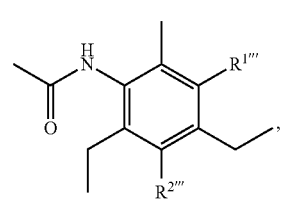

(IV)

wherein either $R^{1'''}$ an acetylamino group and $R^{2'''}$ is bromine or $R^{2'''}$ an acetylamino group and $R^{1'''}$ is bromine,
and/or an isomeric mixture thereof.

21. The process of claim 6, wherein the reacting is conducted at a temperature from 20°C. to 60°C.

* * * * *